United States Patent
Franc et al.

(10) Patent No.: US 9,889,217 B2
(45) Date of Patent: Feb. 13, 2018

(54) DEVICE AND METHOD FOR THE DECONTAMINATION OF HOLLOW OBJECTS SUCH AS CONTAINER CAPS USING UV RADIATIONS

(71) Applicant: CLARANOR, Montfavet (FR)

(72) Inventors: Janyce Franc, Avignon (FR); Eric Houde, Caumont-sur-Durance (FR)

(73) Assignee: CLARANOR, Montfavet (FR)

( * ) Notice: Subject to any disclaimer, the term of this patent is extended or adjusted under 35 U.S.C. 154(b) by 15 days.

(21) Appl. No.: 14/892,770

(22) PCT Filed: May 21, 2014

(86) PCT No.: PCT/EP2014/060443
§ 371 (c)(1),
(2) Date: Nov. 20, 2015

(87) PCT Pub. No.: WO2014/187860
PCT Pub. Date: Nov. 27, 2014

(65) Prior Publication Data
US 2016/0101201 A1    Apr. 14, 2016

(30) Foreign Application Priority Data
May 21, 2013   (EP) .................................... 13305651

(51) Int. Cl.
*A61L 2/00* (2006.01)
*A61L 2/10* (2006.01)
(Continued)

(52) U.S. Cl.
CPC .................... *A61L 2/10* (2013.01); *A61L 2/26* (2013.01); *B08B 7/0057* (2013.01); *B08B 9/08* (2013.01); *B67B 3/003* (2013.01)

(58) Field of Classification Search
CPC .................................... A61L 2/10; B08B 9/08
(Continued)

(56) References Cited

U.S. PATENT DOCUMENTS 3,797,696 A * 3/1974 Dibrell ............... B65D 47/2018
220/714
2004/0219056 A1* 11/2004 Tribelsky ............... B65B 55/16
422/22

(Continued)

FOREIGN PATENT DOCUMENTS

JP         H11-263322 A    9/1999

OTHER PUBLICATIONS

International Search Report from International Patent Application No. PCT/EP2014/060443, dated Nov. 17, 2014.
(Continued)

*Primary Examiner* — Kevin Joyner
(74) *Attorney, Agent, or Firm* — Greer, Burns & Crain, Ltd.

(57) ABSTRACT

A device is provided for the decontamination of hollow objects with a cavity such as caps, including: (i) a first exposure apparatus including at least a UV radiation source and a reflector oriented toward the cavity of the positioned objects, able to produce a direct exposure to UV radiations of surfaces inside the cavity, (ii) a second exposure apparatus including at least a UV radiation source placed on the opposite side relative to the cavity of the positioned objects, the second exposure apparatus being able to expose surfaces inside the objects cavity to UV radiations by diffusion and/or transmission of UV radiations through the walls surrounding the objects cavity, and the first and second exposure apparatus cooperating for producing a global exposure to UV radiations of the surfaces inside the objects cavity. A method is also provided for the decontamination of hollow objects.

18 Claims, 3 Drawing Sheets

(51) Int. Cl.
    *B67B 3/00*     (2006.01)
    *A61L 2/26*     (2006.01)
    *B08B 7/00*     (2006.01)
    *B08B 9/08*     (2006.01)

(58) Field of Classification Search
    USPC .......................................................... 422/24
    See application file for complete search history.

(56) References Cited

U.S. PATENT DOCUMENTS

| | | |
|---|---|---|
| 2006/0225837 A1 | 10/2006 | Haase |
| 2007/0222349 A1* | 9/2007 | Lantis ...................... H01J 61/34 |
| | | 313/12 |
| 2007/0258851 A1 | 11/2007 | Fogg et al. |
| 2012/0134878 A1 | 5/2012 | Silvestri |
| 2013/0193344 A1 | 8/2013 | Drenguis |
| 2013/0272920 A1* | 10/2013 | Knott ...................... A61L 2/087 |
| | | 422/22 |

OTHER PUBLICATIONS

European Search Report from Corresponding European Patent Application No. 13305651.5, dated Oct. 24, 2013.

\* cited by examiner

DEVICE AND METHOD FOR THE DECONTAMINATION OF HOLLOW OBJECTS SUCH AS CONTAINER CAPS USING UV RADIATIONS

BACKGROUND

The invention relates to a device and a method for the decontamination of hollow objects such as container caps by application of ultraviolet (UV) light.

The field of the invention is the decontamination of containers for the packaging in food and drugs industries.

The decontamination of containers by application of pulsed or continuous UV radiations is a well known technique, widely used in particular in the food and medical industry.

The technique exploits the ability of UV radiations to destroy cells and microorganisms, which is essentially due to two effects: a photochemical effect and a photothermal effect.

The photochemical effect, which is obtained with pulsed and continuous UV radiations, results from the absorption by the microorganisms of the UV radiation. It causes breaches and formation of abnormal bonds in the DNA molecules which prevent proper DNA replication. The microorganism's protein production and cell metabolism is blocked and it dies.

The photothermal effect is obtained with pulsed light, and results from the delivery to the microorganism of a high energy in a very short time. The radiations absorbed by the microorganisms causes a steep increase of the internal temperature and breaches of the cells membranes, without heating much the environment.

Decontamination by UV radiations is in particular used in the food industry for the decontamination of containers for food products, such as bottles and caps, prior to their filling. This decontamination is necessary for the good preservation of the packaged products.

The containers are exposed to a UV radiation in the production line, to destroy to the desired extent or level of decontamination the microorganisms on their surfaces.

We know for instance the document US 2007/0258851 from Fogg et al. which discloses a method for sterilizing containers and caps using UV radiations.

One problem with the technique of decontamination by exposure to UV radiations is that all the relevant surfaces must be exposed to an adequate level of radiations, and depending on their shapes and materials (transparent to UV or not), it may be difficult to reach them. This problem becomes even more critical when high levels of decontamination are expected, by example for packaging products with extended duration of conservation. Furthermore, the whole object must be decontaminated, including the internal and external surfaces.

For instance, a level of decontamination of a surface of 5 logs means that no more than 1 over 100000 microorganisms potentially existing on the surface may survive to the process.

For the bottles or similar containers, the problem is solved in the prior art systems by introducing into these bottles light sources or reflectors, and/or using bottles or containers transparent to UV.

The case of caps or any other similar object with a complex or patterned shape is more complex. These objects need also to be decontaminated as they are also in contact with the goods (food, beverages . . . ), but they frequently comprise patterns or shapes which are difficult to expose to UV radiations. Furthermore, they are usually not transparent in the UV, as they are made of materials diffusing and/or absorbing in the UV.

Prior art devices for the decontamination of caps by UV radiations try to solve the problem of the complex shape by providing multiple illumination sources with various angles of incidence, moving the caps relative to the sources or providing and moving reflectors. This classical approach leads to complex systems which are still not satisfactory when high levels of decontamination are expected, because some areas are still not reachable by direct illumination (for instance the plug seal for the water- and air tightness of bottle screw caps).

It is an object of the invention to provide a device and a method for the decontamination of objects such as container caps, which allows high levels of decontamination of all surfaces.

It is another object of the invention to provide a simple, robust and of moderate-cost device for the decontamination of objects such as container caps, which brings a solution to the previously mentioned problems.

It is still another object of the invention to provide a device and a method for such decontamination, adapted for a use in production line.

SUMMARY

Such objects are accomplished with a device for the decontamination of hollow objects which are at least partially translucent to UV radiations and which have a cavity, such as caps, comprising:
  positioning means for positioning the objects into a decontamination zone with the cavity in a predefined orientation,
  first exposure means comprising at least a UV radiation source and/or a reflector for directing a UV radiation, said first exposure means being oriented toward the cavity of the positioned objects and being arranged for producing a direct exposure to UV radiations of surfaces inside said cavity,
characterized in that it further comprises second exposure means comprising at least a UV radiation source and/or a reflector for directing an UV radiation,
  said second exposure means being placed on the opposite side relative to the cavity of said positioned objects, and being arranged for exposing surfaces inside the objects cavity to UV radiations by diffusion and/or transmission of UV radiations through the walls surrounding said objects cavity,
  said first and second exposure means cooperating for producing a global exposure to UV radiations of the surfaces inside said objects cavity.

According to some modes of realization:
  the device of the invention may comprises at least one UV radiation source;
  at least one of the first exposure means and the second exposure means may comprise a UV radiation source.

The first and second exposure means may be able to produce, by combination of their effects, a global exposure to UV radiations of the surfaces inside said objects cavity allowing a global decontamination of the whole objects cavity surface.

The device of the invention may be able to produce a global decontamination of the whole object's cavity surface better than 2 logs.

According to some modes of realization, the device of the invention may further be able to produce a global decontamination of the whole object's cavity surface better than 4 logs, or better than 5 logs.

The device of the invention may further comprises enclosure means for at least partially enclosing the decontamination zone, the positioning means being comprised and/or enclosed in the enclosure means, the enclosure means and the positioning means comprising materials at least partially transparent to UV.

The enclosure means and the positioning means may comprise, and/or be made of, quartz glass.

According to some modes of realization:
the positioning means may comprise tubes of a material at least partially transparent to UV such as quartz, for supporting and/or guiding the objects to be decontaminated,
the tubes of the positioning means may comprise a coolant such as water flowing inside;
the enclosure means may comprise a tube of a material at least partially transparent to UV such as quartz delimitating the decontamination zone and enclosing the positioning means and the object(s) to be decontaminated.

Advantageously:
the enclosure means minimize the risks of contamination from the outside;
the enclosure means and the positioning means let the UV pass through, and so do not create any shadowing effect which could alter the decontamination;
the enclosure means and the positioning means are also decontaminated by the UV, so the decontamination zone as a whole is maintained as clean or sterile as possible.

According to some modes of realization, the device of the invention may further comprise a module including the enclosure means and the positioning means, said module (i) being distinct from the first exposure means and the second exposure means, and (ii) being able to be inserted in the device and/or removed from the device as a whole.

According to some modes of realization, the device of the invention may comprise positioning means with hollow tubes, means for changing the pressure inside said hollow tubes, and means for detecting a pressure change caused by a breakage of said hollow tubes. The positioning means and the enclosure means may comprise quartz tubes.

According to some modes of realization, the device of the invention may comprise positioning means tilted relative the horizontal so as to allow cylindrical object to roll on said positioning means while crossing the decontamination zone.

According to some modes of realization, the device of the invention may further comprise means for inserting the objects in the decontamination zone, so that an object newly inserted on the decontamination zone pushes through the objects already in said decontamination zone and causes the ejection of a decontaminated object from said decontamination zone.

According to some modes of realization, the device of the invention may further comprise a decontamination zone with an elongated shape in a direction of elongation, arranged for containing a plurality of objects. The first exposure means may comprise at least one lamp with a cylindrical shape extending in the direction of elongation, and a reflector with a shape substantially uniform in said direction of elongation facing the cavity of the positioned objects.

The reflector of the first exposure means may be shaped so as to reflect the light from the lamp(s) to the bottom and side parts of the cavity.

The second exposure means may comprise at least one lamp with a cylindrical shape extending in the direction of elongation, and a reflector with a shape substantially uniform in said direction of elongation placed opposite to the cavity of the positioned objects and facing a bottom wall of said cavity.

The reflector of the second exposure means may extend over the bottom wall and the side wall of the object's cavity, and may be shaped to reflect the light from the lamp(s) so as to provide to all parts of said bottom and side walls an illumination with at least light beams having an incidence direction close to the normal of the surface of said walls.

According to some modes of realization, the UV radiation sources of the invention may comprise Xenon flash lamps.

The device of the invention may further comprise at least partially transparent cooling tubes surrounding the UV radiation sources and a fluid coolant circulating in said cooling tubes.

According to some modes of realization, the UV radiation sources of the invention may comprise Excimer lamps.

According to another aspect, the invention comprises a method for the decontamination of hollow objects which are at least partially translucent to UV radiations and which have a cavity such as caps, comprising steps of:
positioning one or several objects into a decontamination zone with the cavity in a predefined orientation,
exposing directly surfaces inside said cavity to UV radiations using first exposure means comprising at least a UV radiation source and/or a reflector for directing an UV radiation,
wherein the method further comprises a step of exposing to UV radiations surfaces inside the objects cavity by diffusion and/or transmission of UV radiations through the walls surrounding said objects cavity, using second exposure means comprising at least a UV radiation source and/or a reflector for directing a UV radiation,
the effects of said first and second exposure means cooperating for producing a global exposure to UV radiations of the surfaces inside said objects cavity.

According to some modes of realization, the steps of exposing surfaces inside the object cavity, using respectively first exposure means and second exposure means, may be executed simultaneously, sequentially, or shifted in time with overlapping exposure periods.

The method of the invention may further comprise a step of masking of external surfaces of the decontaminated object to make it opaque to UV radiations.

It may further comprise at least one of the following steps:
a step of applying a coating on external surfaces,
a step of sticking protective layers on external surfaces.

According to another aspect, the invention comprises the use of the device and/or of the method of the invention for the decontamination of container caps in production line.

The invention also comprises the use of the device for the decontamination of hollow objects, for example caps, comprising materials at least partially translucent in the UV.

As previously explained, objects such as bottle caps, or screw caps are usually not transparent in the visible and/or the UV range of optical wavelengths.

However, some are made of materials which are at least partially translucent in the UV, such as Polypropylene (PP), High-density polyethylene (HDPE), or polyethylene (PE).

So a part of an incident UV radiation is able to pass through their walls, even if it is highly diffused by the surfaces and/or the material.

It is an advantage of the invention to make use of this UV radiation transmitted and/or diffused through the walls for the decontamination of the inner surfaces of the cavity.

The transmission, diffusion, and reflection effects allow indeed bringing light to the narrowest and less accessible structures and shapes in the cavity, through multiple reflections between the surfaces of the cavity.

This diffusion effect is exploited in the invention to its larger extent by illuminating with the second exposure means most of the external surfaces of the objects walls with a broad range of angles of incidence for the light.

The invention is particularly efficient (but not limited to) for reaching high level of decontamination such as 4 log ($10^{-4}$) or 5 log ($10^{-5}$), because it allows avoiding shadow effects or masking effects existing with direct illumination. The second exposure means allow exposing to UV radiation (by transmission and diffusion through the objects walls) the areas which may not be directly accessed by the first exposure means, or exposed to the required amount of radiation (in terms of flux or fluence) with the first exposure means. The second exposure means are dimensioned for that purpose. So, the effects of the first and second exposure means cumulate on all areas to reach the desired amount of exposure to radiations.

Even if it is desired to have caps which are not transparent or translucent to UV for a better conservation of the packaged products, it is still efficient and cost-effective to use caps translucent to the UV, use the device and the method of the invention for the decontamination of these caps, and then apply a protective coating or layer on the external part of the caps for the long-term protection of the products.

BRIEF DESCRIPTION OF THE DRAWINGS

The methods according to embodiments of the present invention may be better understood with reference to the drawings, which are given for illustrative purposes only and are not meant to be limiting. Other aspects, goals and advantages of the invention shall be apparent from the descriptions given hereunder.

DETAILED DESCRIPTION

Figure 1:
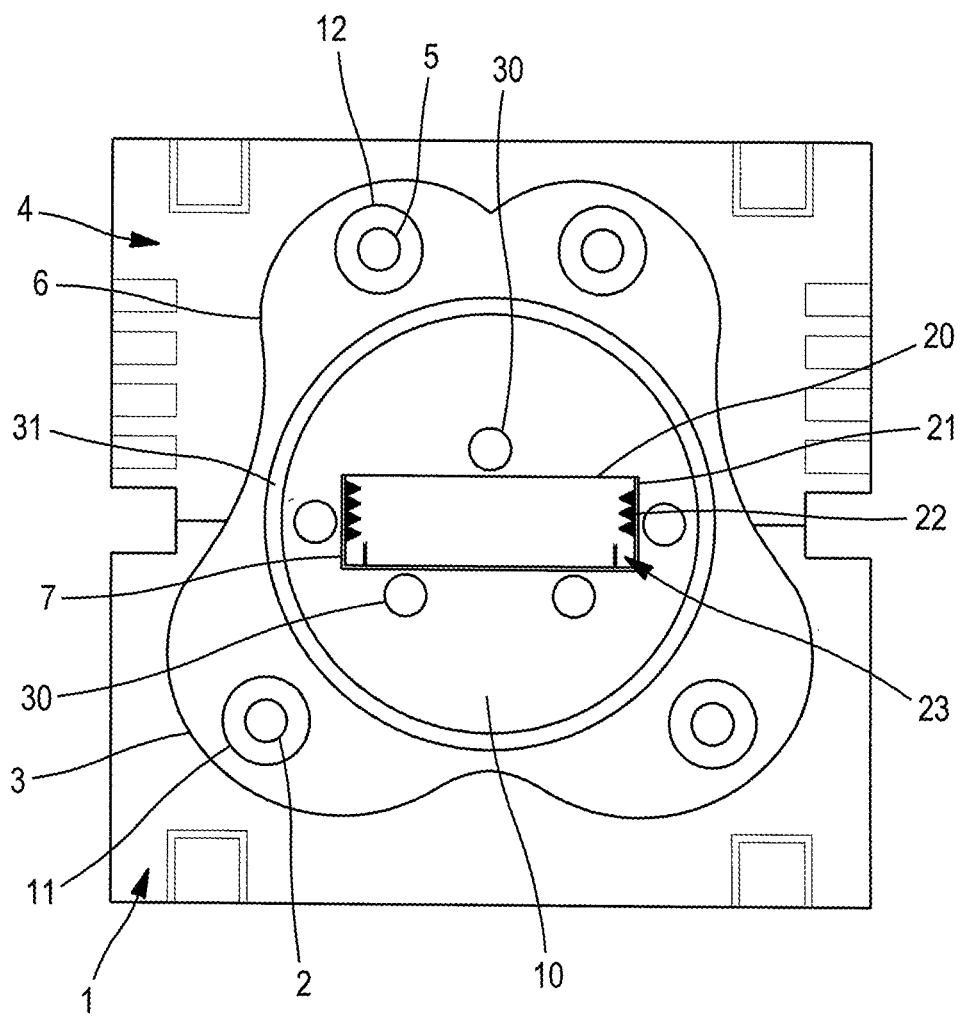
FIG. 1 shows a cut view of a device of the invention according to a mode of realization for the decontamination of bottle caps in production line, FIG. 2(*a*)-(*e*) show examples of propagation of light beams in a device of the invention.

We will now describe, with reference to FIG. 1, an embodiment of the device of the invention for the decontamination of bottle caps 7 in production line.

FIG. 1 shows a cut view of an exemplary bottle screw cap 7. It comprises an internal cavity 20 surrounded by walls 21. The shape of the surfaces inside this cavity 20 is usually complex, comprising for instance a thread 22 for screwing the cap 7 on a bottle and a plug seal 23 for the air and liquid tightness.

The caps 7 are frequently made in materials at least partially translucent to UV radiations, such as for instance Polypropylene (PP), High-density polyethylene (HDPE), or polyethylene (PE).

The device of the invention comprises a decontamination zone 10 elongated in a direction of elongation, in which bottle caps 7 to be decontaminated are inserted.

The decontamination zone 10 is surrounded by first exposure means 4 and second exposure means 1.

The decontamination zone 10 is delimited by a surrounding or enclosing tube 31 extending in the direction of elongation.

The device comprises a plurality of guiding tubes 30, substantially parallel to each other and to the enclosing tube 31, which allow positioning and maintaining the caps 7 during their travel through the decontamination zone 10.

The guiding tubes 30 are enclosed in the enclosing tube 31. The enclosing tube 31 and the guiding tubes 30 are made of a material at least partially translucent or transparent to UV, such as quartz glass. This enclosing tube 31 allows avoiding any contamination of the decontamination zone 10 during normal operation or even when maintenances operations are conducted, for instance on first exposure means 4 or second exposure means 1. So, it allows maximizing the efficiency of the decontamination during normal operation, and also saving time during maintenance as there is no need to decontaminating the decontamination zone 10 after most of maintenance operations.

The caps 7 are inserted at one extremity, relative to a direction of elongation, of the decontamination zone 10, with their cavity 20 oriented toward the second illumination means 4.

The caps 7 are maintained substantially in row in the decontamination zone 10 by the guiding tubes 30. Each newly inserted cap 7 pushes the caps 7 already present in the decontamination zone 10 and causes the last cap 7 to be ejected from the system, in a first-in first-out configuration.

During their travel through the decontamination zone 10, the caps are exposed to the UV radiations from the first exposure means 4 and second exposure means 1, as explained later.

Using guiding tubes 30 allows minimizing the surfaces in contact with the caps 7, and limiting the heat transfers to the caps 7. In the presented embodiment, for example, five guiding tubes 30 are used.

The device of the invention allows decontaminating a continuous flow of caps 7, for instance for use in production line. The exposure to UV of a given cap 7 depends on the time of stay in the decontamination zone 10, which in turn depends on the length of the decontamination zone 10 in the direction of elongation and the travel speed or frequency of insertion of new caps in that decontamination zone 10.

Of course, the exposure to UV of a given cap 7 depends also on the average power of the UV light, and/or on the pulse energy and repetition rate of that UV light.

The decontamination zone 10 comprises parts transparent to UV such as the guiding tubes 30 to ensure a maximal exposure to UV radiations of the caps 7 while guiding them. Absorption is also minimized to avoid excessive heating of the parts in contact with the caps 7.

The second exposure means 1 are designed to illuminate the caps 7 on the external side of the walls 21 surrounding the cavity 20, so as to bring light through these walls 21.

The second exposure means 1 comprise two xenon flash lamps 2. These lamps 2 comprise a glass tube filled with a gas such as xenon, with electrodes at either end. When submitted to a high voltage pulse, the gas ionizes and conducts to produce a high intensity light pulse with optical wavelengths ranging from UV to near infrared (NIR), for instance from 200 to 1100 nm.

The lamps 2 are surrounded by a cooling tube 11 in which a liquid coolant such as water is circulating. This cooling system allows evacuating the heat generated by the lamps 2. The cooling tube 11 is made of quartz glass.

The lamps 2 and the cooling tube 11 are substantially parallel to the direction of elongation of the decontamination zone 10.

The second exposure means 1 are symmetrical relative to a median plan crossing the center of the decontamination area 10 and parallel to the direction of elongation of the decontamination area 10.

The flash lamps 2 are located on either side of the median plan. They are surrounded by a reflector 3.

The reflector 3 is made in an aluminum piece, machine-cut to the required shape and polished. The shape of the reflector 3 is substantially invariant by translation in the direction of elongation of the decontamination zone 10.

The reflector 3 is made of portions of conics. It comprises two parts, each one surrounding a lamp 2, which extend over the bottom wall and the side wall 21 of the cap 7. The reflector 3 is shaped so as to provide to all parts of the bottom and side walls 21 an illumination with at least light beams having an incidence direction close to the normal of the surface, or having moderate or small incidence angles, smaller than 45 degrees relative to the normal of the surface.

Of course, the side and bottom walls 21 are also crossed by light beams with any other angle of incidence, but the design of the reflector 3 ensures an optimal illumination of all parts.

The first exposure means 4 are designed to illuminate the caps 7 on the cavity side 20, so as to bring light directly into the cavity 20.

The first exposure means 4 comprise also two xenon flash lamps 5. The lamps 5 are surrounded by a cooling tube 12 in which a liquid coolant such as water is circulating. This cooling system allows evacuating the heat generated by the lamps 5. The cooling tube 12 is made of quartz glass.

The lamps 5 and the cooling tube 12 are substantially parallel to the direction of elongation of the decontamination zone 10.

The first exposure means 4 are symmetrical relative to a median plan crossing the center of the decontamination area 10 and parallel to the direction of elongation of the decontamination area 10.

The flash lamps 5 are located on either side of the median plan. They are surrounded by a reflector 6.

The reflector 6 are made in an aluminum piece, machine-cut to the required shape and polished. The shape of the reflector 6 is substantially invariant by translation in the direction of elongation of the decontamination zone 10.

The reflector 6 is made of portions of conics. It comprises two parts, each one surrounding a lamp 5, facing the cavity 20 of the cap 7. The reflector 6 is shaped so as to bring the light issued from the lamps 5 to the bottom and side parts of the cavity 20.

As previously explained, the first illumination means 4 alone are not able to product a direct exposure to UV radiations of all surfaces inside the cavity 20 which is comprehensive and uniform enough to reach a high level of decontamination. In particular, shadowing effects may affect the efficiency of the process in the thread 21 and the plug seal 23 areas. This may happen even if the material is translucent to UV, because of the effects of the diffusing surfaces and of the local angles of incidence of the light on these surfaces.

The second illumination means 1 provide a complementary, quite uniform illumination through all the parts of the walls 21.

So the effects of the first and second illumination means combine to provide a global exposure to UV radiations of all parts of the cavity's 20 inner surfaces sufficient for the decontamination purpose.

FIG. 2(a)-(e) show examples of ray-tracing of light beams propagating in the decontamination zone 20.

Figure 2:
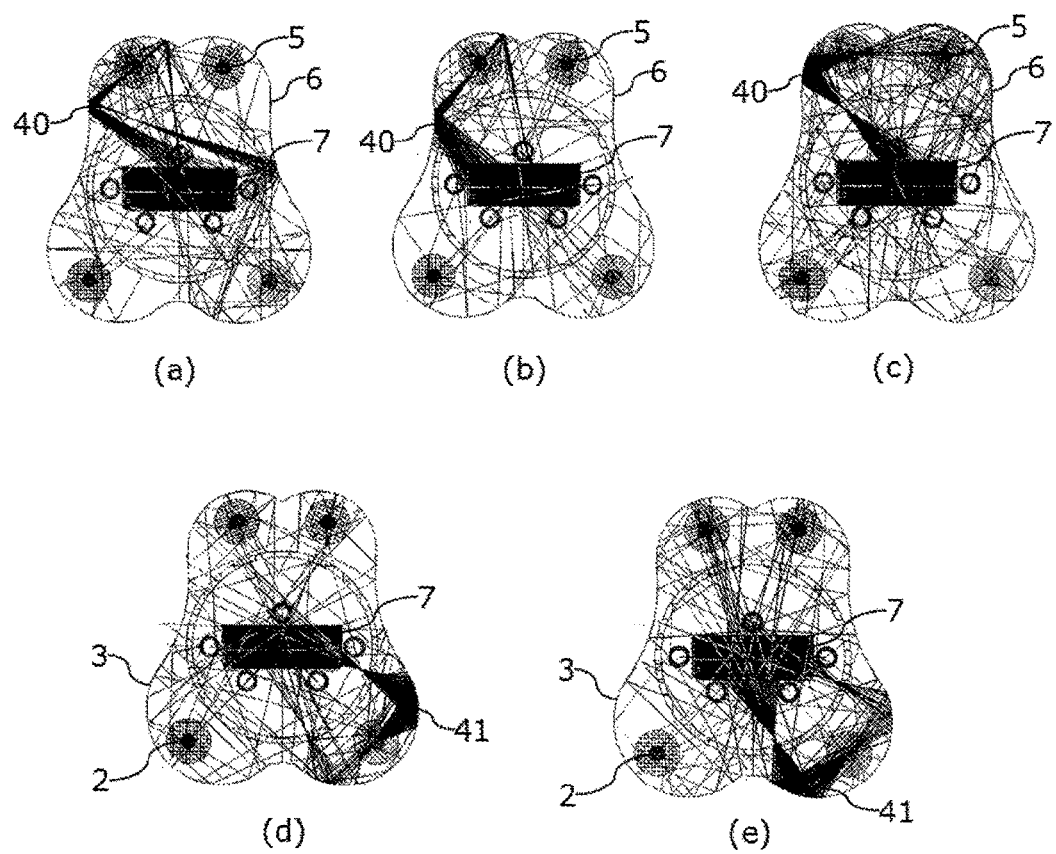

FIG. 2(a)-(c) show ray-tracing of light beams 40 issued from the flash-lamp 5 of the first exposure means 4, showing how the side and bottom walls 21 of the internal cavity 20 of the cap 7 may be illuminated with beams having small incidence angles.

FIG. 2(d)-(e) show ray-tracing of light beams 41 issued from the flash-lamp 2 of the second exposure means 1, showing how the outside walls 21 of the cap 7 may be illuminated with beams having small incidence angles.

It should also be noted that the light from each of the lamps 2, 5 undergoes multiples reflections on the reflectors 3 and 6 and on the cap's walls 21. The result is a substantially uniform and diffuse illumination in the decontamination zone 20, which improves the efficiency of the device.

The reflectors 3 and 6 actually combine to form a continuous surface surrounding the decontamination zone 20, with a shape optimized to bring illumination to any possible part of the cap 7.

It is an advantage of the invention that all internal and external surfaces of caps 7, and all parts of decontamination area 10 in contact with the caps 7 such as the guiding tubes 30, are exposed to UV and so decontaminated simultaneously. This allows minimizing the risk of re-contamination of the caps 7 after leaving the decontamination zone 10.

Figure 3:
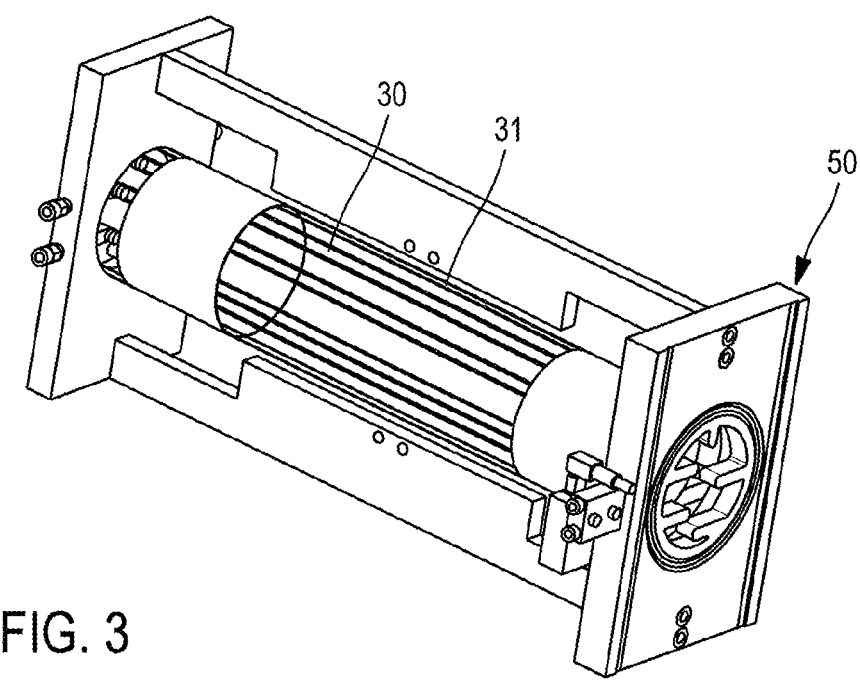
FIG. 3 shows a perspective view of the decontamination zone of the device of the invention.

With reference to FIG. 3, the enclosing tube 31 delimitating the decontamination zone 10 and the guiding tubes 30 are assembled so as to constitute a module 50, or a cartridge 50. This module 50 is distinct from the first exposure means 4 and the second exposure means 1, and it can be inserted or removed as a whole. Such modular configuration allows optimizing the maintenance process. For instance, the module 50 can be removed during maintenance to limit the contamination risks. In can also be easily sterilized elsewhere, and easily changed.

The device further comprises means for detecting a breakage of the guiding tubes 30. The guiding tubes 30 are made with hollow quartz tubes 30, which are connected in an airtight way to a vacuum system. If a guiding tube 30 is broken, a leak appears in the vacuum circuit. So, by monitoring the pressure in the vacuum circuit, such breakage can be detected.

The device further comprises means such as tube connectors for injecting a peroxide gas in the enclosing tube 31 of the module 50. So, the decontamination zone 10 and the guiding tubes 30 can be sterilized, even when the module 50 is mounted on the device. The advantage of using peroxyde gas is that it does not leave marks or deposits on the quartz pieces.

Figure 4:
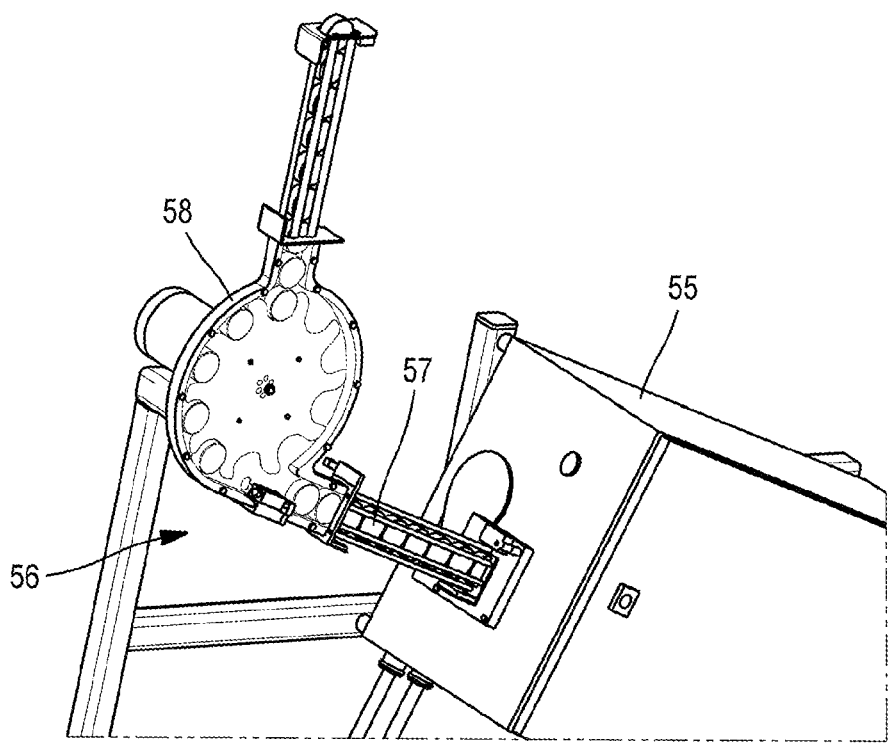
FIG. 4 shows a device of the invention inserted in a production line.

With reference to FIG. 4, the device further comprises means 56 for inserting the caps 7 in the decontamination zone 10, located in a box unit 55.

The decontamination zone 10 is tilted relative to the horizontal direction so that the caps 7 may also progress in the decontamination zone 10 under the effect of gravity, and roll on their side during their progression so as to be exposed to the UV radiations evenly, on their entire circumference.

This allows avoiding contact areas between neighboring caps 7 which would otherwise not be correctly decontaminated.

The means 56 for inserting the caps 7 comprise guiding rails 57, which are also tilted relative to the horizontal direction so that the caps 7 may progress on them under the effect of gravity, rolling on their side.

The means 56 for inserting the caps 7 further comprise a distribution wheel 58 for inserting the caps 7 in the guiding rails 57. This distribution wheel 58 allows avoiding any unwanted pressure on the caps 7 in the decontamination zone 10, due to the flow of incoming caps coming from the production line.

According to some modes of realization:
- the guiding tubes 30 may further comprise a coolant flowing inside;
- the guiding elements 30 may be rods. They also may be of any shape;
- the enclosing tube 31 may be of any shape.

According to some modes of realization, the reflector 3 of the first exposure means 1 and/or the reflector 6 of the second exposure means may comprise:
- any material;
- two separate pieces, or two separate reflecting surfaces;
- plates in aluminium or any other material folded to shape.

According to some modes of realization, only the first or second illumination means may comprise lamps, the uniform illumination effect being achieved through multiples reflections on the reflectors 3 and 6 on both sides of the cap 7.

While this invention has been described in conjunction with a number of embodiments, it is evident that many alternatives, modifications and variations would be or are apparent to those of ordinary skill in the applicable arts. Accordingly, it is intended to embrace all such alternatives, modifications, equivalents and variations that are within the spirit and scope of this invention.

The invention claimed is:

1. A device for the decontamination of hollow objects which are at least partially translucent to UV radiations and which have a cavity, the device comprising:
   - positioning means with hollow tubes for positioning the objects into a decontamination zone with their cavity in a predefined orientation;
   - pressure means for changing the pressure inside said hollow tubes, and detecting means for detecting a pressure change caused by a breakage of said hollow tubes;
   - first exposure means comprising at least a UV radiation source and/or a reflector for directing a UV radiation, said first exposure means being oriented toward the cavity of the positioned objects and being arranged for producing a direct exposure to UV radiations of surfaces inside said cavity;
   - second exposure means comprising at least a UV radiation source and/or a reflector for directing UV radiation;
   - said second exposure means being placed on the opposite side relative to the cavity of said positioned objects and being arranged for exposing surfaces inside the objects cavity to UV radiations by diffusion and/or transmission of UV radiations through the walls surrounding said objects cavity; and
   - said first and second exposure means cooperating for producing a global exposure to UV radiations of the surfaces inside said objects cavity.

2. The device of claim 1, which is able to produce a global decontamination of the whole object's cavity surface better than 2 logs.

3. The device of claim 1, which further comprises enclosure means for at least partially enclosing the decontamination zone, the positioning means being comprised and/or enclosed in the enclosure means, the enclosure means and the positioning means comprising materials at least partially transparent to UV.

4. The device of claim 3, which further comprises a module including the enclosure means and the positioning means, said module (i) being distinct from the first exposure means and the second exposure means, and (ii) being able to be inserted in the device and/or removed from the device as a whole.

5. The device of claim 1, which comprises positioning means tilted relative the horizontal so as to allow cylindrical objects to roll on said positioning means while crossing the decontamination zone.

6. The device of claim 1, which further comprises means for inserting the objects in the decontamination zone, so that an object newly inserted on the decontamination zone pushes through the objects already in said decontamination zone and causes the ejection of a decontaminated object from said decontamination zone.

7. The device of claim 1, which further comprises a decontamination zone with an elongated shape in a direction of elongation, arranged for containing a plurality of objects.

8. The device of claim 7, in which the first exposure means comprise at least one lamp with a cylindrical shape extending in the direction of elongation, and a reflector with a shape substantially uniform in said direction of elongation facing the cavity of the positioned objects.

9. The device of claim 8, in which the reflector of the first exposure means is shaped so as to reflect the light from the lamp(s) to the bottom and side parts of the cavity.

10. The device of claim 7, in which the second exposure means comprises at least one lamp with a cylindrical shape extending in the direction of elongation, and a reflector with a shape substantially uniform in said direction of elongation placed opposite to the cavity of the positioned objects and facing a bottom wall of said cavity.

11. The device of claim 10, in which the reflector of the second exposure means extends over the bottom wall and the side wall of the object's cavity, and is shaped to reflect the light from the lamp(s) so as to provide to all parts of said bottom and side walls an illumination with at least light beams having an incidence direction close to the normal of the surface of said walls.

12. The device of claim 1, in which the UV radiation sources comprise Xenon flash lamps.

13. The device of claim 12, which further comprises at least partially transparent cooling tubes surrounding the UV radiation sources and a fluid coolant circulating in said cooling tubes.

14. The device of claim 1, in which the UV radiation sources comprise Excimer lamps.

15. A method for the decontamination of hollow objects which are at least partially translucent to UV radiations and which have a cavity, the method comprising steps of:
   - positioning one or several objects into a decontamination zone with the cavity in a predefined orientation using hollow tubes connected to a vacuum circuit;
   - monitoring a pressure in the vacuum circuit;

exposing directly surfaces inside said cavity to UV radiations using first exposure means comprising at least a UV radiation source and/or a reflector for directing UV radiation;

exposing surfaces inside the objects cavity to UV radiations by diffusion and/or transmission of UV radiations through the walls surrounding said objects cavity, using second exposure means comprising at least a UV radiation source and/or a reflector for directing UV radiation; and the effects of said first and second exposure means cooperating for producing a global exposure to UV radiations of the surfaces inside said objects cavity.

16. The method of claim 15, in which the steps of exposing surfaces inside the object cavity are executed simultaneously.

17. The method of claim 15, which further comprises a step of masking of external surfaces of the decontaminated object to make it opaque to UV radiations.

18. A use of the device and/or of the method according to claim 15 for the decontamination of container caps in a production line.

* * * * *